_(12)_ United States Patent  
Pivetti et al.

(10) Patent No.: US 8,163,922 B2  
(45) Date of Patent: Apr. 24, 2012

(54) PROCESS FOR THE PREPARATION OF 8-HYDROXY-5-[(1R)-1-HYDROXY-2[[(1R)-2-(4-METHOXYPHENYL)-1-METHYL-ETHYL]AMINO]ETHYL]-2(1H)-QUINOLINONE MONOHYDROCHLORIDE

(75) Inventors: Fausto Pivetti, Parma (IT); Monica Bocchi, Parma (IT); Maurizio Delcanale, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 273 days.

(21) Appl. No.: 12/512,187

(22) Filed: Jul. 30, 2009

(65) Prior Publication Data

US 2009/0326231 A1 Dec. 31, 2009

Related U.S. Application Data

(63) Continuation of application No. PCT/IB2008/000134, filed on Jan. 22, 2008.

(30) Foreign Application Priority Data

Jan. 30, 2007 (EP) ..................................... 07001950

(51) Int. Cl.  
*C07D 215/38* (2006.01)

(52) U.S. Cl. ..................................................... 546/156

(58) Field of Classification Search .................. 546/156; 514/312

See application file for complete search history.

(56) References Cited

U.S. PATENT DOCUMENTS 4,579,854 A * 4/1986 Iwakuma et al. ............. 514/312  
2007/0197586 A1 8/2007 Pivetti et al.

FOREIGN PATENT DOCUMENTS

EP 0 147 719 7/1985

OTHER PUBLICATIONS

U.S. Appl. No. 12/436,322, filed May 6, 2009, Pivetti, et al.  
U.S. Appl. No. 12/436,368, filed May 6, 2009, Pivetti, et al.  
"List of psychotropic substances under international control", International Narcotics Control Board, Vienna International Centre, Vienna Austria, Green List, Annex to the annual statistical report on psychotropic substances (form P), 23$^{rd}$ Ed., Aug. 2003, pp. 3-4.

* cited by examiner

*Primary Examiner* — D M Seaman  
(74) *Attorney, Agent, or Firm* — Oblon, Spivak, McClelland, Maier & Neustadt, L.L.P.

(57) ABSTRACT

8-hydroxy-5-[(1R)-1-hydroxy-2[[(1R)-2-(4-methoxyphenyl)-1-methylethyl]amino]ethyl]-2(1H)-quinolinone monohydrochloride of formula (I) may be conveniently prepared in a diastereomeric pure form from optically pure precursors that are readily available by simple resolution and asymmetric reduction.

22 Claims, No Drawings

PROCESS FOR THE PREPARATION OF 8-HYDROXY-5-[(1R)-1-HYDROXY-2[[(1R)-2-(4-METHOXYPHENYL)-1-METHYL-ETHYL]AMINO]ETHYL]-2(1H)-QUINOLINONE MONOHYDROCHLORIDE

CROSS REFERENCES TO RELATED APPLICATIONS

This application is a continuation of International Patent Application No. PCT/IB2008/000134, filed on Jan. 22, 2008, and claims priority to European Patent Application No. 07001950.0, filed on Jan. 30, 2007, both of which are incorporated herein by reference in their entireties.

BACKGROUND OF THE INVENTION

1. Field of the Invention

The present invention relates to processes for the preparation of 8-hydroxy-5-[(1R)-1-hydroxy-2[[(1R)-2-(4-methoxyphenyl)-1-methylethyl]amino]ethyl]-2(1H)-quinolinone monohydrochloride. The present invention also relates to intermediates which are useful in such a process.

2. Discussion of the Background 8-hydroxy-5-[(1R)-1-hydroxy-2 [[(1R)-2-(4-methoxyphenyl)-1-methylethyl]amino]ethyl]-2(1H)-quinolinone monohydrochloride (I) is disclosed in EP 0 147 719 as a bronchodilator provided with a potent beta-2-adrenoceptor stimulating action.

The compound, that has also been referred to as 8-hydroxy-5-{(1R)-1-hydroxy-2-{N-((1R)-2-(p-methoxyphenyl)-1-methylethyl)amino]ethyl}carbostyril hydrochloride and TA 2005, is identified hereinafter for the sake of convenience also with the code CHF4226.

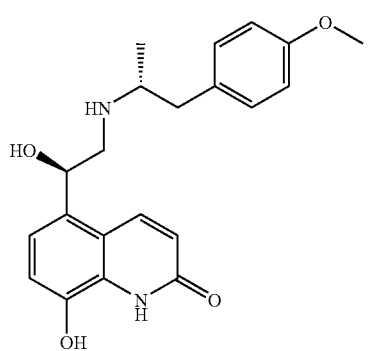
(I)

EP 0 147 719 describes a process for the preparation of TA2005, including within its scope all four optical isomers and mixture thereof. The process consists of the halogenation or oxidation of a compound of the formula (VII):

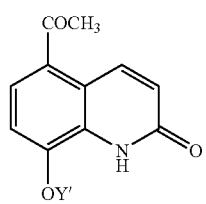
(VII)

to give respectively a compound of the formula (VIII) or (IX), where X is halogen atom and Y'O— is hydroxyl or a conventionally protected hydroxyl,

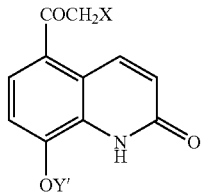
(VIII)

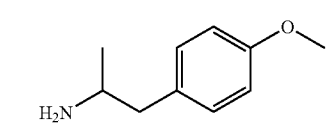
(IX)

which by reaction with N-(2-(p-methoxyphenyl)-1-methylethyl)-amine of formula (X)

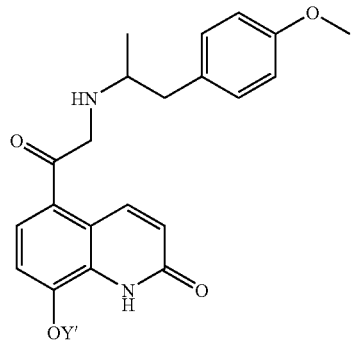
(X)

gives a compound of formula (II') or (III'):

(II')

(III')

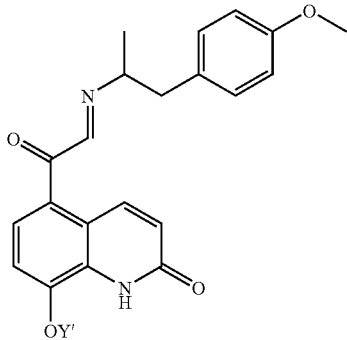

which are reduced by reaction with a reducing agent to give the compound (IV').

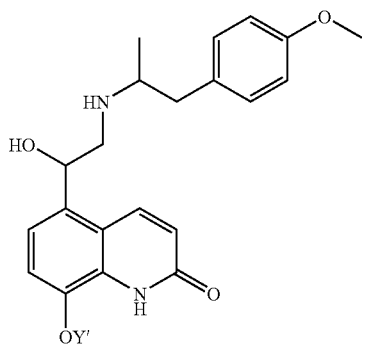

The compound (IV') is obtained in the form of a mixture of two stereoisomers, (i.e., α- or β-isomers, constituted by a mixture of (R),(R)- and (S),(S)-isomers thereof or a mixture of (R),(S)- and (S),(R)-isomers thereof) that must be separated into each of the optical isomers of the compound (IV') through a lengthy and time consuming method. Compound (I) is then obtained by the removal of the protecting group by catalytic hydrogenation of compound (IV').

The process for the preparation of (I) according to Tanabe patent shows some problems and disadvantages. For example, compound (X) is considered a psychostimulant and hallucinogen, classified among psychotropic substances in many countries, therefore its preparation and use is regulated by very restrictive rules which makes its employment difficult without particular authorisations. Moreover, its preparation, disclosed on page 16, preparation 3 of EP 0 147 719, requires reagents of difficult preparation such as α-methyl-α-nitro-p-methoxystyrene and (S)-1-(2-naphthylsulfonyl)pyrrolidine-2-carboxylic acid.

In addition, the process for resolution, through fractional crystallization, seems quite difficult, especially for the use of many solvents or solvent mixtures, such as methanol, or ethyl acetate and isopropanol and of uncommon and expensive resolving agents, such as (S)-1-(2-naphthylsulfonyl)pyrrolidine-2-carboxilic acid. Furthermore, the reported yield, after crystallization, is very low, about 35%.

Moreover the synthesis of compound (I) according to EP 0 147 719 requires two hydrogenation steps, both carried out with catalytic Pd/C hydrogenation conditions to obtain (X) from its precursor, α-methyl-α-nitro-p-methoxystyrene and to deprotect the phenolic group during the conversion of (IV') to (I).

Therefore there is a need to develop a process for the preparation of CHF4226 which does not have all the above mentioned drawbacks of the prior art and in particular there is a need to develop a process leading to the desired CHF4226 having the (R),(R) configuration.

SUMMARY OF THE INVENTION

Accordingly, it is one object of the present invention to provide novel processes for preparing CHF4226.

It is another object of the present invention to provide novel processes for preparing CHF4226 of the (R),(R) configuration.

It is another object of the present invention to provide novel processes for preparing CHF4226, which are practical and efficient.

It is another object of the present invention to provide novel processes for preparing CHF4226 of the (R),(R) configuration, which are practical and efficient.

It is another object of the present invention to provide novel intermediates which are useful in such a process.

These and other objects, which will become apparent during the following detailed description, have been achieved by the inventors' discovery of processes which utilize optically pure precursors that are readily available by simple resolution and asymmetric reduction, and immediately lead to the correct (R),(R) configuration of compound (I), resulting in a simpler procedure having higher yields.

Thus, the present invention provides a more convenient process for preparing CHF4226 alternative to the one disclosed in EP 0147 719 with a simpler methodology, comprising the following steps according to scheme 1:

(a) reacting a compound of formula (XII):

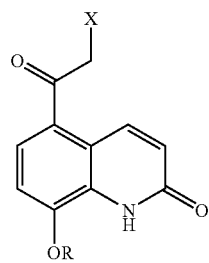

wherein X is an halogen atom selected from the group consisting of fluorine, chlorine, bromine, and iodine and R is a hydroxyl-protecting group, with a compound of formula (X'):

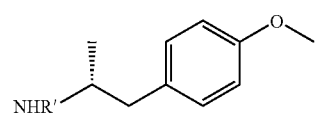

wherein R' is an amino-protecting group, to obtain a compound of formula (XIII):

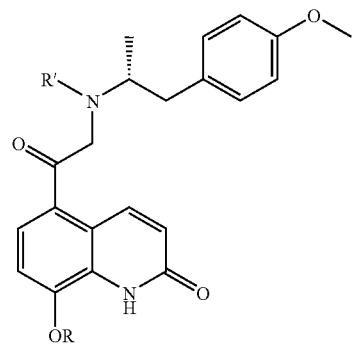

(b) reducing said compound of formula (XIII) to obtain a compound of formula (XIV):

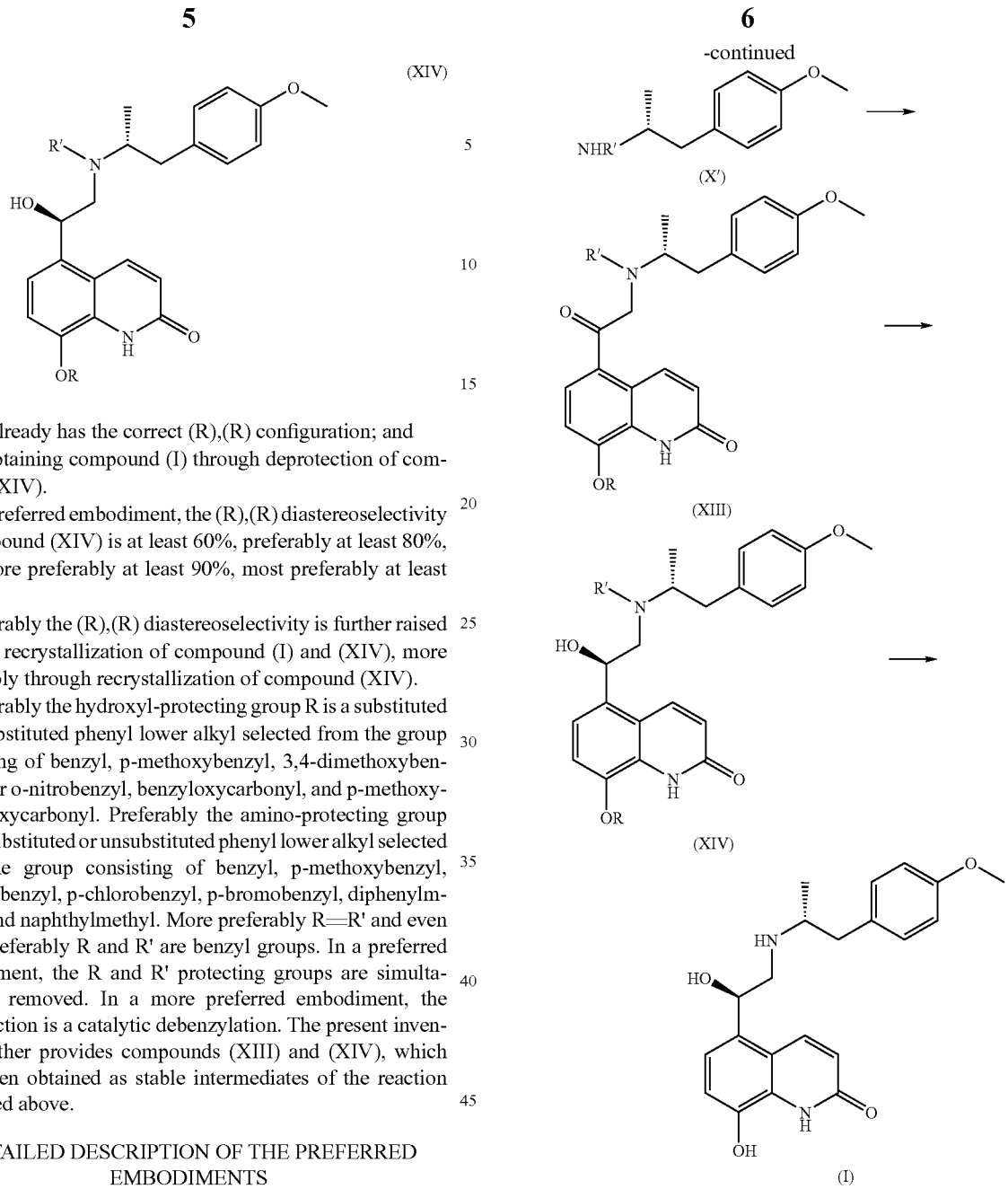

which already has the correct (R),(R) configuration; and (c) obtaining compound (I) through deprotection of compound (XIV).

In a preferred embodiment, the (R),(R) diastereoselectivity of compound (XIV) is at least 60%, preferably at least 80%, even more preferably at least 90%, most preferably at least 95%.

Preferably the (R),(R) diastereoselectivity is further raised through recrystallization of compound (I) and (XIV), more preferably through recrystallization of compound (XIV).

Preferably the hydroxyl-protecting group R is a substituted or unsubstituted phenyl lower alkyl selected from the group consisting of benzyl, p-methoxybenzyl, 3,4-dimethoxybenzyl, p- or o-nitrobenzyl, benzyloxycarbonyl, and p-methoxybenzyloxycarbonyl. Preferably the amino-protecting group R' is a substituted or unsubstituted phenyl lower alkyl selected from the group consisting of benzyl, p-methoxybenzyl, p-fluorobenzyl, p-chlorobenzyl, p-bromobenzyl, diphenylmethyl, and naphthylmethyl. More preferably R=R' and even more preferably R and R' are benzyl groups. In a preferred embodiment, the R and R' protecting groups are simultaneously removed. In a more preferred embodiment, the deprotection is a catalytic debenzylation. The present invention further provides compounds (XIII) and (XIV), which have been obtained as stable intermediates of the reaction described above.

DETAILED DESCRIPTION OF THE PREFERRED EMBODIMENTS

The present invention provides a process for preparing CHF4226, comprising the following steps:

Scheme 1

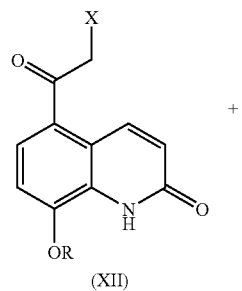

(a) reacting a compound of formula (XII), wherein R is a hydroxyl-protecting group, with a compound of formula (X') wherein X is an halogen atom selected from the group consisting of fluorine, chlorine, bromine, and iodine and R' is an amino-protecting group, to obtain a compound of formula (XIII);

(b) reducing said compound, to obtain a compound of formula (XIV) already bearing the correct (R),(R) configuration; and (c) obtaining compound (I) through deprotection of compound (XIV).

The (R),(R) diastereoselectivity of compound (XIV) is at least 60%, preferably at least 80%, even more preferably at least 90%, most preferably at least 95%.

Preferably, the (R),(R) diastereoselectivity is further raised through recrystallization of compound (I) and (XIV), more preferably through recrystallization of compound (XIV) using known methods.

In the context of the present invention, the term "protecting group" means a group which protects one or more functional groups of a compound giving rise to a protected derivative of the specified compound. Functional groups which may be protected include, by way of example, amino groups, hydroxyl groups, and the like. Protecting groups are well-known to those skilled in the art and are described, for example, in T. W. Greene and G. M. Wuts, *Protecting Groups in Organic Synthesis*, Third Edition, Wiley, New York, 1999, and references cited therein.

The term "amino-protecting group" means a protecting group suitable for preventing undesired reactions at an amino group. Representative amino-protecting groups include, but are not limited to, tert-butoxycarbonyl (BOC), trityl (Tr), benzyloxycarbonyl (Cbz), 9-fluorenylmethoxycarbonyl (FMOC), formyl, trimethylsilyl (TMS), tert-butyldimethylsilyl (TBS), benzyl, p-methoxybenzyl, p-fluorobenzyl, p-chlorobenzyl, p-bromobenzyl, diphenylmethyl naphtylmethyl, and the like.

The term "hydroxyl-protecting group" means a protecting group suitable for preventing undesirable reactions at a hydroxyl group. Representative hydroxyl-protecting groups include, but are not limited to, silyl groups including tri(1-6C)-alkylsilyl groups, such as trimethylsilyl (TMS), triethylsilyl (TES), tert-butyldimethylsilyl (TBS), and the like; esters (acyl groups) including (1-6C)-alkanoyl groups, such as formyl, acetyl, and the like; arylmethyl groups, such as benzyl (Bn), p-methoxybenzyl (PMB), 9-fluorenylmethyl (Fm), diphenylmethyl (benzhydryl, DPM), and the like.

In the present invention, R is preferably a substituted or unsubstituted phenyl lower alkyl selected from the group consisting of benzyl, p-methoxybenzyl, 3,4-dimethoxybenzyl, p- or o-nitrobenzyl, benzyloxycarbonyl and p-methoxybenzyloxycarbonyl, and R' is a substituted or unsubstituted phenyl lower alkyl preferably selected from the group consisting of benzyl, p-methoxybenzyl, p-fluorobenzyl, p-chlorobenzyl, p-bromobenzyl, diphenylmethyl, and naphthylmethyl. More preferably R is the same as R' and even more preferably R and R' are both benzyl groups.

In a preferred embodiment, the R and R' protecting groups are simultaneously removed. In a more preferred embodiment the deprotection is a catalytic debenzylation.

In particular, a compound of formula (XII) is reacted with an optically pure compound of formula (X') to obtain an optically pure intermediate (XIII). The compound of formula (XII) may be obtained by any method known in the art. For example, it may be obtained from a compound of formula (VII) through various halogenation procedures, as described in Example 13 of EP 0 147 719.

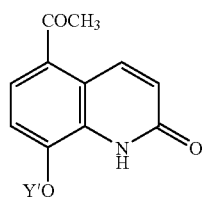

(VII)

The optically pure compound (X'), may be obtained by resolution of the racemic compound with (L)- or (D)-mandelic acid in presence of an alcoholic solvent such as methanol (MeOH), using a suitable modification, known to those skilled in the art, of the procedure of Kraft, et al., *Reec. Trav. Chim. Pays-Bas*, 85, 607 (1966).

The reaction of (XII) and (X') is performed in a suitable solvent or solvent mixture such as dichloromethane or its mixture with dimethylformamide and a suitable alkaline agent such as sodium hydrogen carbonate.

Compound (XIII) contains both an amino protecting group and a hydroxyl-protecting group of the type described above. A stable compound (XIII) may be isolated as salt, preferably as the hydrochloride salt.

The reduction of the intermediate (XIII) may be carried out with a suitable reducing agent such as lithium borohydride, sodium cyanoborohydride, sodium monoacetoxyborohydride, borane complexes, and preferably sodium borohydride in a solvent such as methanol, ethanol, 2-propanol, tetrahydrofuran, ether, diglyme, dichloromethane and mixtures thereof. Preferably, methanol and dichloromethane are used to obtain the compound of formula (XIV) with the required (R),(R) absolute configuration and good diastereoselectivity.

The compound of formula (XIV) may be isolated as free base or, alternatively, as a crystalline salt formed by reaction with a suitable acid, such as tartaric acid, mandelic acid and preferably hydrochloric acid, using various solvents, such as methanol, ethanol, 2-propanol, water, acetone, tetrahydrofuran, dichloromethane and mixtures thereof.

The (R),(R) diastereomeric purity of compound (XIV) is at least 60%, preferably at least 80%, even more preferably at least 90%, most preferably at least 95%.

The deprotection of (XIV) to give compound (I) is performed in presence of a catalyst with a solvent. Preferably, the solvent is methanol, ethanol, 2-propanol, water, tetrahydrofuran, or mixtures thereof, and preferably ethanol, at a temperature of 0 to 100° C. and more preferably of 10 to 30° C. Preferably, the catalyst is selected from the group of palladium-BaCO$_3$, palladium black, and even more preferably palladium-charcoal.

Compound (I) is obtained with a (R),(R) diastereoisomeric purity of at least 60%, preferably of at least 80%, even more preferably of at least 90%, most preferably of at least 95%.

The (R),(R) diastereoisomeric purity of compound (XIV) may be further raised through recrystallization or suspension of (XIV) or preferably its salt, more preferably its hydrochloride salt in a solvent, such as methanol, ethanol, 2-propanol, water, acetone, tetrahydrofuran, dichloromethane and mixtures thereof.

The (R),(R) diastereoisomeric purity of compound (I) may be also raised by recrystallization of compound (I), for example through the method described in WO 2005/089760.

According to a preferred embodiment, compound (XIII) contains R' which is a benzyl group.

This process is advantageous as compared to the process described in EP 0 147 719, in which the intermediate (V), with the undesired (S,R) absolute configuration, is formed early and requires later inversion, thereby lengthening the process.

The deprotection of the amino group is often a quite slow reaction which requires particular catalysts or reaction conditions (es. unreduced palladium-charcoal, high temperatures and hydrogen pressure), according to T. W. Greene and G. M. Wuts, *Protecting Groups in Organic Synthesis*, Third Edition, Wiley, New York, 1999, and references cited therein. Stressed reaction conditions could cause over-reduction of (I) giving rise to impurities.

In the present invention, the presence in compound (XIV) of a vicinal hydroxyl group favours the N-deprotection reaction. The reaction is achieved quite sharply and under mild conditions, therefore preventing the formation of overreduced impurities.

Moreover, in a preferred embodiment, since the N-benzyl moiety of 4-methoxy-α-methyl-N-(benzyl)-benzeneethanamine(L)-(+)-mandelate is maintained during the synthesis, the final catalytic hydrogenation step allows the simultaneous deprotection of both the amino and hydroxyl groups, leading to compound (I).

According to the most preferred embodiment, R═R'═benzyl, and R and R' are removed simultaneously through a debenzylation reaction.

Other features of the invention will become apparent in the course of the following descriptions of exemplary embodiments which are given for illustration of the invention and are not intended to be limiting thereof.

EXAMPLES

Example 1

Synthesis of 5-[[[(1R)-2-(4-methoxyphenyl)-1-methylethyl]-(phenylmethyl)amino]acetyl]-8-(phenylmethoxy)-(1H)-quinolin-2-one hydrochloride (XIII), wherein R and R'=benzyl 5-(α-bromo)acetyl-8-benzyloxy-2(1H)-quinolinone (XII) (20 g, 0.053 mol) and (R)-4-methoxy-α-methyl-N-(benzyl)-benzeneethanamine (X') (20.6 g, 0.08 mol) are suspended in dichloromethane (250 ml) and dimethylformamide (50 ml). Sodium hydrogencarbonate (17 g) is added, and the mixture is refluxed overnight. Inorganic salts are filtered, then the solution is concentrated, diluted with chloroform (800 ml), and washed with aqueous hydrogen chloride ca. 10% w/w (2×250 ml). The organic phase is washed with brine (300 ml), dried ($Na_2SO_4$), filtered, and concentrated in a rotary evaporator. The oily residue is combined with acetone (100 ml) and stirred at T=5° C., excess (R)-4-methoxy-α-methyl-N-(benzyl)-benzeneethanamine, as the hydrochloride salt, crystallized from the mixture and is filtered, with washing with acetone. The filtered solution is concentrated, and the residue is suspended in ethyl acetate, filtered, and dried, to give (XIII) (28.0 g, 91% yield) as hydrochloride salt.

(XIII) monohydrochloride (8.8 g) is suspended in ethyl acetate (160 ml) and heated to 78 to 80° C.; to the refluxing mixture ethanol (50 ml) is slowly added until dissolution is complete. The solution is cooled to 5° C. and kept cold for 60 hours; the crystallized product is filtered, washed with ethyl acetate (50 ml) and petroleum ether (50 ml), then it is dried under vacuum at T=50° C. Crystallized (XIII) monohydrochloride is recovered as a pale yellow powder.

Example 2

Synthesis of [5-[(1R)-1-hydroxy-2-[[(1R)-2-(4-methoxyphenyl)-1-methylethyl](phenylmethyl)amino]ethyl]-8-phenylmethoxy)-2(1H)-quinolinone] (XIV), wherein R and R'=benzyl (XIII) monohydrochloride (5.0 g, 8.6 mmol) is dissolved in a mixture of dichloromethane (100 ml) and methanol (50 ml), then the solution is cooled to T=60° C. Sodium borohydride (2.0 g, 52 mmol) is added portion-wise under nitrogen atmosphere while keeping T<−40° C., and the mixture is stirred for 30 minutes, then T is raised to −10° C., and water (500 ml) is added keeping T<10° C. The aqueous phase is separated and extracted with further chloroform (100 ml), the organic phases are mixed and washed with aqueous hydrogen chloride ca. 10% w/w (500 ml), then dried ($Na_2SO_4$), filtered, and concentrated in a rotary evaporator. To the residual solution (ca. 30 ml) ethyl acetate (100 ml) is added, and the solution is concentrated again, then ethyl acetate (50 ml) is added causing crystallization of crude (XIV) as hydrochloride salt. The suspension is kept cold (T=5° C.) overnight, then it is filtered, and the solid is dried under vacuum at T=50° C. (4.3 g, 86% yield). The diastereoisomeric purity (R),(R)/[(R),(R)+(S),(R)] is determined as 90%.

2 g of crude (XIV) monohydrochloride are suspended in acetone (80 ml) and heated to T=58 to 80° C., water (16 ml) is added until dissolution was complete. The solution is cooled to 5° C. and kept cold overnight; the crystallized (XIV) monohydrochloride is filtered and dried under vacuum at T=50° C. Crystallized (XIV) is recovered as a white solid. The diastereoisomeric purity is determined as 99%.

Example 3

Synthesis of 8-hydroxy-5-[(1R)-1-hydroxy-2-{[(1R)-2-(4-methoxyphenyl)-1-methylethyl]amino}ethyl]-2(1H)-quinolinone hydrochloride (1), wherein R and R'=benzyl

[5-[(1R)-1-hydroxy-2-[[(1R)-2-(4-methoxyphenyl)-1-methylethyl]-(phenylmethyl)amino]ethyl]-8-phenylmethoxy)-2(1H)-quinolinone hydrochloride (XIV) (600 mg, 1.0 mmol) is suspended in ethanol (10 ml) and water (0.5 ml) in a Parr flask. Pd/C5% (100 mg, 50% wet) is added, and the mixture is hydrogenated at T=20° C. for 1.5 hours. The mixture is filtered through a celite pad, washed with ethanol (10 ml), and the filtered solution is concentrated in a rotary evaporator. Into the warm (T=40° C.) residual solution (ca. 5 ml) di-isopropylether (5 ml) is slowly added drop-wise, causing precipitation of (1), which is filtered and dried under vacuum at T=50° C. (I) is recovered as a white powder.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A process for preparing a compound of formula (I):

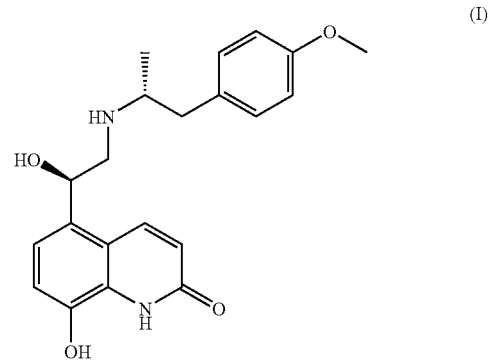

(I)

or a salt thereof, comprising:
(a) reacting a compound of formula (XII):

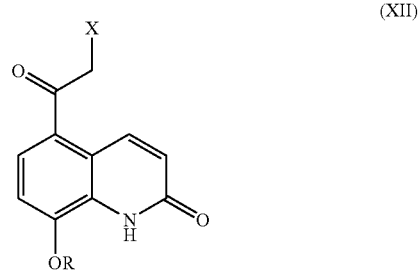

(XII)

wherein X is an halogen atom selected from the group consisting of fluorine, chlorine, bromine, and iodine, and R is a hydroxyl-protecting group, with a compound of formula (X'):

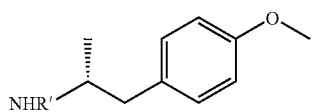
(X')

wherein R' is an amino-protecting group, to obtain a compound of formula (XIII):

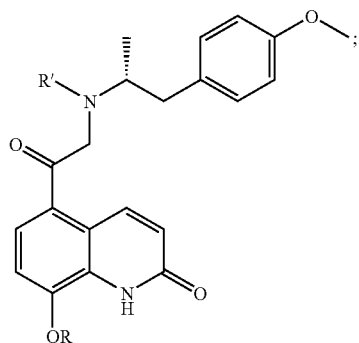
(XIII)

(b) reducing said compound of formula (XIII), to obtain a compound of formula (XIV):

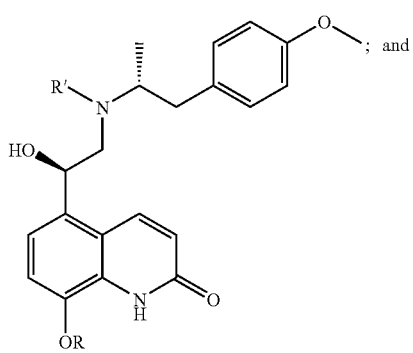
(XIV)

(c) deprotecting said compound of formula (XIV), to obtain said compound of formula (I).

2. A process according to claim 1 wherein the (R),(R) diastereoselectivity of said compound (I) is at least 60%.

3. A process according to claim 1 wherein the (R),(R) diastereoisomeric purity of said compound (I) is at least 80%.

4. A process according to claim 1 wherein the (R),(R) diastereoisomeric purity of said compound (I) is at least 90%.

5. A process according to claim 1 wherein the (R),(R) diastereoisomeric purity of said compound (I) is at least 95%.

6. A process according to claim 1, wherein the (R),(R) diastereoisomeric purity of compound (XIV) is at least 60%.

7. A process according to claim 1, wherein the (R),(R) diastereoisomeric purity of compound (XIV) is at least 80%.

8. A process according to claim 1, wherein the (R),(R) diastereoisomeric purity of compound (XIV) is at least 90%.

9. A process according to claim 1, wherein the (R),(R) diastereoisomeric purity of compound (XIV) is at least 95%.

10. A process according to claim 1, further comprising recrystallizing said compound of formula (XIV) prior to said deprotection.

11. A process according to claim 1, further comprising recrystallizing said compound of formula (I).

12. A process according to claim 1, wherein R is substituted or unsubstituted phenyl lower alkyl selected from the group consisting of benzyl, p-methoxybenzyl, 3,4-dimethoxybenzyl, p-nitrobenzyl, o-nitrobenzyl, benzyloxycarbonyl, and p-methoxybenzyloxycarbonyl.

13. A process according to claim 1, wherein R' is a substituted or unsubstituted phenyl lower alkyl selected from the group consisting of benzyl, p-methoxybenzyl, p-fluorobenzyl, p-chlorobenzyl, p-bromobenzyl, diphenylmethyl, and naphtylmethyl.

14. A process according to claim 1, wherein R is the same as R'.

15. A process according to claim 14, wherein R and R' are both benzyl.

16. A process according to claim 1, wherein the R and R' protecting groups are simultaneously removed.

17. A compound of formula (XIII):

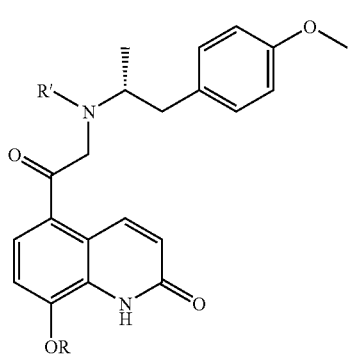
(XIII)

wherein R is a hydroxyl-protecting group and R' is a substituted or unsubstituted phenyl lower alkyl selected from the group consisting of benzyl, p-methoxybenzyl, p-fluorobenzyl, p-chlorobenzyl, p-bromobenzyl, diphenylmethyl, and naphtylmethyl.

18. A compound according to claim 17, wherein R is substituted or unsubstituted phenyl lower alkyl selected from the group consisting of benzyl, p-methoxybenzyl, 3,4-dimethoxybenzyl, p-nitrobenzyl, o-nitrobenzyl, benzyloxycarbonyl, and p-methoxybenzyloxycarbonyl.

19. A compound according to claim 17, wherein R and R' are both benzyl.

20. A compound of formula (XIV):

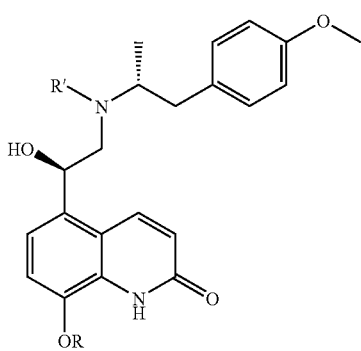
(XIV)

wherein R is a hydroxyl-protecting group and R' is a substituted or unsubstituted phenyl lower alkyl selected from the group consisting of benzyl, p-methoxybenzyl, p-fluorobenzyl, p-chlorobenzyl, p-bromobenzyl, diphenylmethyl, and naphtylmethyl.

21. A compound according to claim 20, wherein R is substituted or unsubstituted phenyl lower alkyl selected from the group consisting of benzyl, p-methoxybenzyl, 3,4-dimethoxybenzyl, p-nitrobenzyl, o-nitrobenzyl, benzyloxycarbonyl, and p-methoxybenzyloxycarbonyl.

22. A compound according to claim 21, wherein R and R' are both benzyl.

* * * * *